United States Patent
Flanagan et al.

(10) Patent No.: US 11,957,347 B2
(45) Date of Patent: Apr. 16, 2024

(54) DEVICES, SYSTEMS, AND METHODS FOR TORQUE AMPLIFICATION IN MEDICAL SYSTEMS

(71) Applicant: Boston Scientific Scimed Inc., Maple Grove, MN (US)

(72) Inventors: Aiden Flanagan, County Galway (IE); Stephen McCooey, Dundalk (IE); Martin Lawrence Fawdry, Galway (IE)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 18/169,026

(22) Filed: Feb. 14, 2023

(65) Prior Publication Data
US 2023/0293174 A1  Sep. 21, 2023

Related U.S. Application Data

(60) Provisional application No. 63/310,424, filed on Feb. 15, 2022.

(51) Int. Cl.
*A61B 17/072* (2006.01)
*A61B 17/29* (2006.01)

(52) U.S. Cl.
CPC .......... *A61B 17/07207* (2013.01); *A61B 2017/07271* (2013.01); *A61B 2017/2927* (2013.01)

(58) Field of Classification Search
CPC .......... A61B 17/29; A61B 18/1447; A61B 2017/292; A61B 2017/2927; A61B 2017/2912; A61B 2017/2902; A61B 2017/2913; A61B 2017/00314; A61B 2090/035; A61B 2017/00973; A61B 2090/3762; A61B 2017/2908; A61B 2090/374; A61B 2017/2932; A61B 2018/1226; A61B 2017/2938; A61B 2017/2925

See application file for complete search history.

(56) References Cited

U.S. PATENT DOCUMENTS

| | | |
|---|---|---|
| 5,176,688 A | 1/1993 | Narayan et al. |
| 9,724,162 B2 | 8/2017 | Crainich et al. |
| 10,786,272 B2 | 9/2020 | Beira |
| 10,881,422 B2 | 1/2021 | Kim et al. |
| 2006/0161185 A1 | 7/2006 | Saadat et al. |
| 2012/0310111 A1 | 12/2012 | Shachar et al. |
| 2017/0290602 A1* | 10/2017 | Germain ............... A61B 34/74 |
| 2020/0078087 A1 | 3/2020 | Miyazaki et al. |

* cited by examiner

*Primary Examiner* — Nathaniel C Chukwurah
(74) *Attorney, Agent, or Firm* — Bookoff McAndrews, PLLC

(57) ABSTRACT

A medical device may include a main shaft extending from a proximal end to a distal end; an actuator at a proximal portion of the medical device; an end effector positioned at a distal end of the main shaft and comprising a first jaw and a second jaw; a motor; and a torque amplification system. The torque amplification system may include a driveshaft coupled to the motor; a spring coupled to the driveshaft and configured to expand or contract in a proximal or a distal direction relative to the driveshaft; a hammer moveably coupled to the driveshaft; and an anvil coupled to the end effector and abutting the hammer. The anvil may be configured to provide a rotational power output to the end effector to move the first jaw and/or the second jaw.

20 Claims, 7 Drawing Sheets

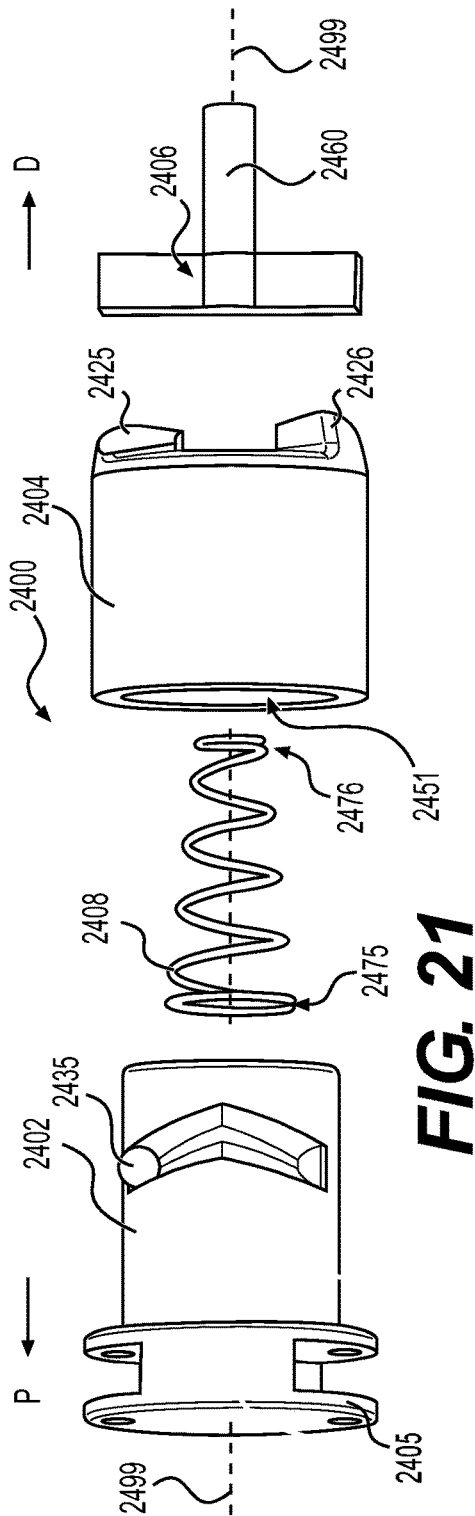
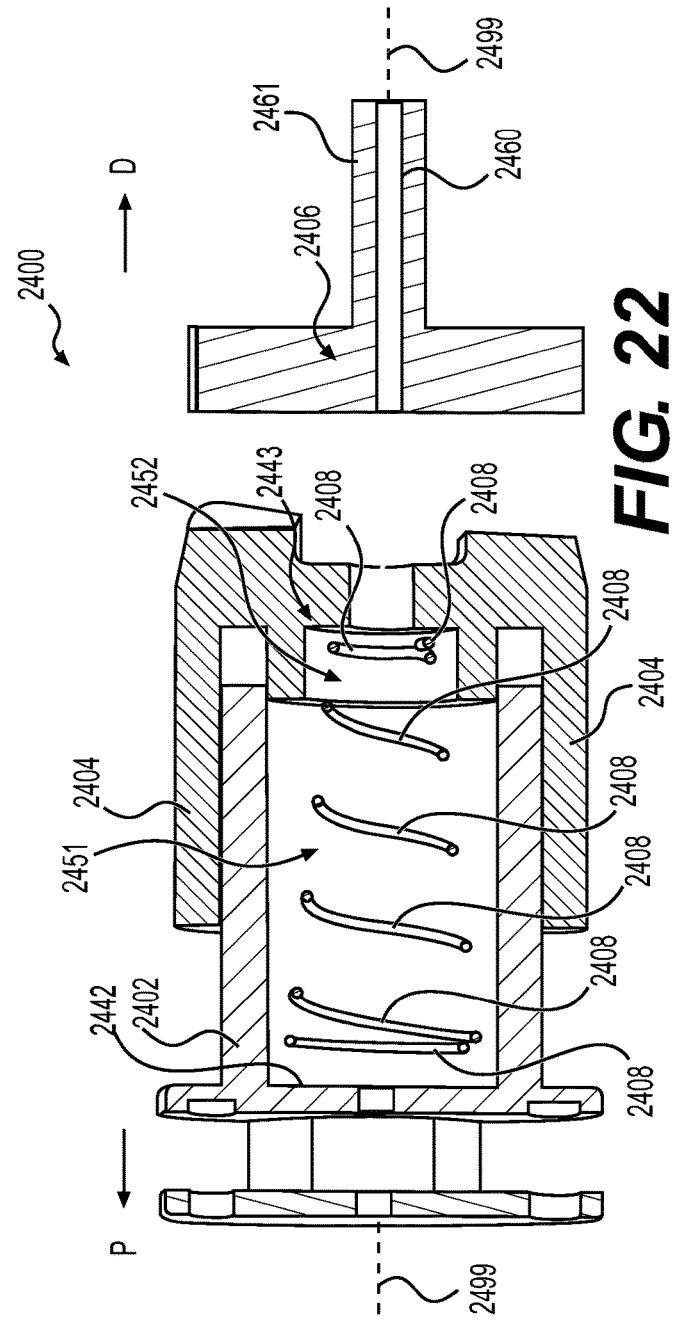

DEVICES, SYSTEMS, AND METHODS FOR TORQUE AMPLIFICATION IN MEDICAL SYSTEMS

CROSS-REFERENCE TO RELATED APPLICATIONS

This application claims the benefit of priority of U.S. Provisional Patent Application No. 63/310,424, filed Feb. 15, 2022, the entirety of which is incorporated herein by reference

TECHNICAL FIELD

This disclosure generally relates to medical systems, devices, and related methods that may be used to treat a subject. Aspects of the disclosure relate to medical systems, devices, and methods for medical procedures, such as actuating one or more medical devices during an endoscopic procedure, among other aspects.

BACKGROUND

Technological developments have given users of medical systems, devices, and methods the ability to conduct increasingly complex procedures on subjects. For example, the robotization of medical procedures may provide multiple advantages and potential new capabilities that lead to better quality healthcare, more efficient procedures, new interventions, faster surgeon training, and reduced re-hospitalizations for repeat procedures. The technologies that will enable the trend toward robotization are still in need of development. For example, endoluminal surgical tools present several challenges for the robotization, such as the small scale required for the technology and the unique requirements for tools to operate on a human. In one example, in order to actuate any instrument or tool at a distal end of a catheter device, such as a grasper, a force needs to be applied in a controlled and directed manner of sufficient force for the tool to be effective. In addition, the duration of a procedure may be increased due to the need to manually re-actuate a device in order to apply the appropriate level of force to a patient. Furthermore, manual actuation may increase strain on the device operator. There is a need for improvements in micro-actuation technology of catheter devices and other endoluminal surgical tools for cutting, grabbing, collecting, and otherwise manipulating tissue, among other uses.

The systems, devices, and methods of this disclosure may rectify some of the deficiencies described above or address other aspects of the art.

SUMMARY

Examples of the disclosure relate to, among other things, systems, devices, and methods for performing one or more medical procedures with the medical systems and devices. Each of the examples disclosed herein may include one or more of the features described in connection with any of the other disclosed examples.

In one example, a medical device may include a main shaft extending from a proximal end to a distal end; an actuator at a proximal portion of the medical device; an end effector positioned at a distal end of the main shaft and comprising a first jaw and a second jaw; a motor; and a torque amplification system. The torque amplification system may include a driveshaft coupled to the motor; a spring coupled to the driveshaft and configured to expand or contract in a proximal or a distal direction relative to the driveshaft; a hammer moveably coupled to the driveshaft; and an anvil coupled to the end effector and abutting the hammer. The anvil may be configured to provide a rotational power output to the end effector to move the first jaw and/or the second jaw.

In other aspects, the medical device may include one or more of the following features. The motor may be positioned within a distal portion of the main shaft. The medical device may further include a handle coupled to the proximal end of the main shaft, and the actuator may be positioned on the handle. The end effector may be an endoscopic stapler, a grasper, forceps, or scissors. The hammer may include a first flange extending distally from a distal face of hammer; the anvil may include a second flange extending proximally from a proximal face of the anvil; and the first flange may be configured to engage the second flange to rotate anvil about a central longitudinal axis of the anvil. The hammer may be cylindrical and may include an inner tubular portion; the inner tubular portion may include a channel extending transverse to a central longitudinal axis of the hammer; the driveshaft may include a ball bearing coupled to a distal end of the driveshaft; and the ball bearing may be movably positioned within the channel. The spring may extend circumferentially around a radially-outer surface of the driveshaft and abut a proximal end of the inner tubular portion. The torque amplification system may further include a central, longitudinal lumen extending through the driveshaft, the hammer, the spring, and the anvil. Each of the hammer and the anvil may be cylindrical; and the hammer may have a diameter substantially the same as the diameter of the anvil. The driveshaft may include (i) a recess extending longitudinally through the driveshaft from a distal end of the driveshaft, and (ii) a pair of channels extending proximally from the distal end; the spring may be positioned with the recess; and the hammer may include (i) a pair of protrusions extending proximally from a proximal face of the hammer, wherein each of the pair of protrusions are configured to be received by each of the pair of channels, respectively; and (ii) a pair of flanges extending distally from a distal end face of hammer.

In other aspects, the medical device may include one or more of the following features. The anvil may be T-shaped. The driveshaft may include a first recess; the hammer may include a second recess and a pair of protrusions extending distally from a distal face of the hammer; the spring may be positioned within the first recess and a distal end of the spring may be fixedly coupled to a proximally-facing surface within the second recess; and a distal portion of the driveshaft may be received within the second recess. The hammer may include a first channel within the second recess; the driveshaft may include a second channel in a radially-outward surface, relative to a central longitudinal axis, of the driveshaft; and a ball bearing may be positioned between the first channel and the second channel. The spring may be conical. A ratchet mechanism may be coupled to the driveshaft.

In other aspects, a medical device may include an end effector; and a torque amplification system. The torque amplification system may include a driveshaft coupled to the motor; a spring coupled to the driveshaft and configured to expand or contract in a proximal or a distal direction relative to the driveshaft; a hammer moveably coupled to the driveshaft; an anvil coupled to an output shaft and abutting the hammer, wherein the anvil is configured to provide a rotational power output to the output shaft; and a lumen extending along a central longitudinal axis of the torque amplification system, wherein the lumen extends through the driveshaft, the spring, the hammer, and the anvil. The output shaft may be coupled to the end effector.

In other aspects, the medical device may include one or more of the following features. The hammer may be cylindrical and include an inner tubular portion; the inner tubular portion may include a channel extending transverse to a central longitudinal axis of the hammer; the driveshaft may include a ball bearing coupled to a distal end of the driveshaft; the ball bearing may be movably positioned within the channel; and the spring may extend circumferentially around a radially-outer surface of the driveshaft and abut a proximal end of the inner tubular portion.

In other aspects, the medical device may include one or more of the following features. The driveshaft may include (i) a recess extending longitudinally through the driveshaft from a distal end of the driveshaft, and (ii) a pair of channels extending proximally from the distal end; the spring may be positioned with the recess; and the hammer may include (i) a pair of protrusions extending proximally from a proximal face of the hammer. Each of the pair of protrusions may be configured to be received by each of the pair of channels, respectively; and (ii) a pair of flanges extending distally from a distal end face of hammer. The driveshaft may include a first recess; the hammer may include a second recess, a pair of protrusions extending distally from a distal face of hammer, and a first channel within the second recess; the spring may be positioned within the first recess and a distal end of the spring may be fixedly coupled to a proximally-facing surface within the second recess; a distal portion of the driveshaft may be received within the second recess; the driveshaft may include a second channel in a radially-outward surface, relative to a central longitudinal axis, of the driveshaft; and a ball bearing may be movably positioned between the first channel and the second channel.

In other aspects, a medical device may include a shaft extending longitudinally from a proximal end portion to a distal end portion; a motor positioned within the distal end portion; an end effector at the distal end portion; and a torque amplification system. The torque amplification system may include a driveshaft coupled to the motor; a spring coupled to the driveshaft and configured to move relative to the driveshaft; a hammer moveably coupled to the driveshaft; and an anvil coupled to the end effector and abutting the hammer, wherein the anvil is configured to provide a rotational power output to the end effector.

It may be understood that both the foregoing general description and the following detailed description are exemplary and explanatory only and are not restrictive of this disclosure, as claimed.

BRIEF DESCRIPTION OF THE DRAWINGS

The accompanying drawings, which are incorporated in and constitute a part of this specification, illustrate exemplary aspects of this disclosure and together with the description, serve to explain the principles of this disclosure.

FIG. 21 illustrates a side view of another torque amplification system in a partially-disassembled state, according to aspects of this disclosure.

FIG. 22 illustrates a side, cross-sectional view of the torque amplification system of FIG. 21, according to aspects of this disclosure.

DETAILED DESCRIPTION

Figures 1, 2:
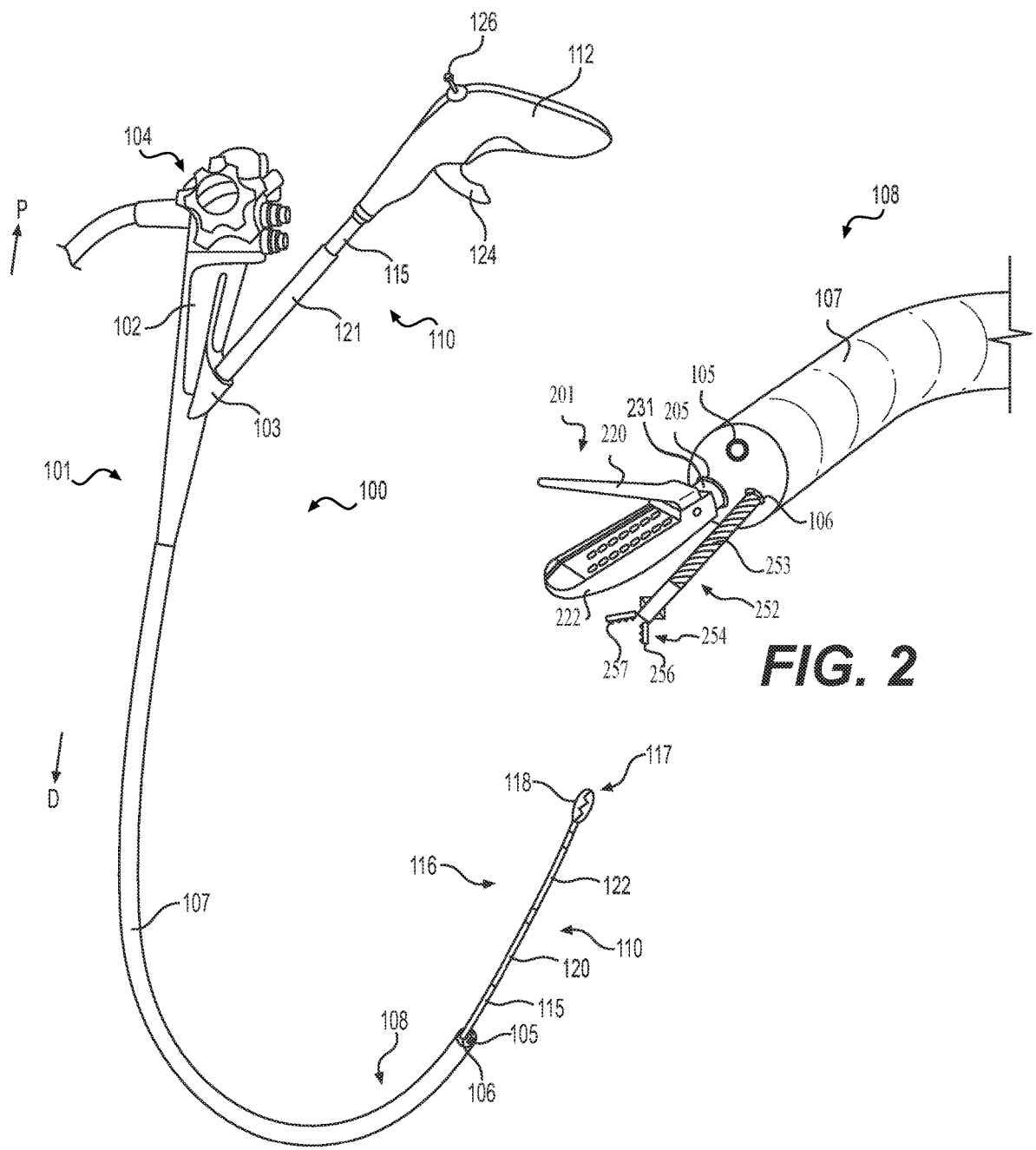
FIG. 1 illustrates a perspective view of a medical device system, according to aspects of this disclosure.
FIG. 2 illustrates a distal portion of the medical device system of FIG. 1, according to aspects of this disclosure.

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. Proximal and distal directions are labeled with arrows marked "P" and "D", respectively, throughout the figures. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Embodiments of this disclosure include devices, systems, and methods for manipulating, cutting, stapling, grabbing, and/or otherwise treating tissue. In some examples, the devices, systems and/or methods discussed herein may be utilized during endoscopic medical procedures, such as endoscopic mucosal resection (EMR) and/or endoscopic submucosal dissection (ESD) procedures. In examples, a procedure may include endoluminal placement of a medical device proximate to a target area within the body of a patient. Placement of the medical device may be via a catheter, scope (endoscope, bronchoscope, colonoscope, gastroscope, duodenoscope, etc.), tube, or sheath, inserted into the GI tract via a natural orifice or incision. The orifice can be, for example, the nose, mouth, or anus, and the placement can be in any portion of the GI tract, including the esophagus, stomach, duodenum, large intestine, or small intestine. Placement also can be in other organs reachable via the GI tract or otherwise via an incision. The patient's tissue may be manipulated via the medical device, such as grasping tissue, stapling tissue, and/or cutting tissue for subsequent removal from the patient's body. In other examples, the devices, systems, and methods may be incorporated into a needle apparatus used to pierce tissue, and may be implemented to apply a translational force on the needle to facilitate piercing tissue. In some other examples, the devices, systems, and methods of this application may be used to facilitate articulation of a distal end of a catheter device, for example to facilitate movement of tissue via contact with a distal end of a catheter.

Reference will now be made in detail to examples of this disclosure described above and illustrated in the accompanying drawings. Wherever possible, the same reference numbers will be used throughout the drawings to refer to the same or like parts.

FIG. 1 illustrates a perspective view of an exemplary medical device assembly 100 including an endoscope 101 and a medical device 110. Although medical device assembly 100 is shown with endoscope 101, any other similar insertion device may be used in medical device assembly 100, such as a bronchoscope, colonoscope, gastroscope, duodenoscope, etc. Endoscope 101 may include a handle 102, actuators 104, and a body 107 extending from handle 102 to a distal end 108. A working channel 106 may extend from a working channel port 103 positioned on the handle 102 to an opening at distal end 108. Distal end 108 of endoscope 101 may also include a camera 105, and movement of distal end 108 and/or functionality of camera 105 may be controlled via one or more actuators 104 on handle 102. Medical device 110 may be configured to be inserted into working channel 106 of endoscope 101.

Medical device 110 may include a handle 112, a main shaft 115 extending from the handle 112 to a distal portion 116 of medical device 110, and a grasper 118 at a distal end 117 of the device. Handle 112 may include actuators 124, 126, and shaft 115 may extend through a connector 121 at working channel port 103. Connector 121 may be directly coupled to working channel port 103 of endoscope 101. In other examples, medical device 110 may not include connector 121. Shaft 115 may extend from handle 112 through connector 121 into working channel 106 of endoscope 101, and may be movable within working channel 106. Shaft 115 may extend longitudinally a length larger than the longitudinal length of endoscope 101, such that once shaft 115 is delivered through working channel 106, a portion of shaft 115 extends distally from a distal opening of working channel 106 (shown in FIG. 1). Distal portion 116 of medical device 110 may include a first articulation shaft 120, a second articulation shaft 122, and a grasper 118 at a distal end 117 of medical device 110. In other examples, medical device 110 may not include both first articulation shaft 120 and a second articulation shaft 122. For example, medical device 110 may only include a single articulation shaft 120, 122 or may not include an articulation shaft 120, 122 and shaft 115 may extend to grasper 118. Articulation shafts 120, 122 may be moveable via one or more actuators 124, 126 of handle 112.

Grasper 118 may open and close via actuation of one or more actuators 124, 126 of handle 112. Medical device 110 may include a motor 310 (shown in FIG. 3) positioned within medical device 110, and grasper 118 may move between an open position and a closed position via actuation of motor 310. For example, as discussed in greater detail below, motor 310 may be coupled to a gear assembly configured to move grasper 118 from a closed position to an open position, and from an open position to a closed position. For example, the gear assembly may translate a rotational output of motor 310 to a translational output moving one of or both jaws or portions of grasper 118 to transition between an open position to a closed position, and from the closed position to the open position. In some examples, motor 310 may be a micro-motor positioned within main shaft 115 or one or more articulation shafts 120, 122. One or more of actuators 124, 126 may be electronically coupled to motor 310 via one or more electrical wires or wirelessly, and one or more actuators 124, 126 may control the output of motor 310 in order to open or close grasper 118.

FIG. 2 illustrates distal end 108 of endoscope 101 with camera 105 and two different medical devices 201, 252 positioned within two different working channels 106, 205 of endoscope 101. In one aspect, medical device 201 may be a medical stapler device 201, and medical device 252 may be a grasper 252. Each of medical stapler device 201 and grasper 252 may be positioned in working channel 205 and working channel 106, respectively. Grasper 252 includes a longitudinal shaft 253 and an end effector 254, including jaws 256, 257. In the same manner as described above with relation to medical device 110, a motor (e.g., motor 310) may be positioned within shaft 253 and may actuate end effector 254 to move jaws 256, 257 towards or away from each other to transition between an open configuration and a closed configuration.

Medical stapler device 201 includes a longitudinal shaft 231, a stapler body 222, and an anvil 220. Stapler body 222 may contain a plurality of staples with a cartridge (not shown), and each of the plurality of staples may be configured to be deployed from stapler body 222. A motor (e.g., motor 310) may be positioned within stapler body 222, anvil 220, and/or shaft 231, and the motor may be configured to actuate medical stapler device 201 to move stapler body 222 and anvil 220 towards or away from each other to transition between an open configuration and a closed configuration. In some examples, a motor (e.g., motor 310) may be used to deploy staples, or other fasteners, from stapler body 222. Although only medical stapler device 201 and grasper 252 are shown in FIG. 2, the devices, systems and methods of this disclosure may be incorporated into any other medical device for insertion into a patient's body or for otherwise acting on a patient's body. For example, the devices, systems, and methods discussed in this application may be incorporated into an endoscopic snare device, a cutting device (e.g., endoscopic scissors or other devices for movement of one or more cutting elements), endoscopic burs, cleaning brushes, ligation devices, biopsy forceps, suturing systems, or any other device or system known in the art.

The torque amplification systems discussed in this application generally relate to systems for increasing the amount of torque applied to a rotational output of a motor within a medical device, such as a micro-motor within a medical device. One example of a torque amplification system is an impact driver system that may include a spring-driven mechanism that applies rotational striking blows to a rotational output shaft. Each of the rotational striking blows has a larger torque than the input torque provided to the impact driver system, such as an input of a rotational force supplied by a motor. Further details of torque amplification systems and how the systems operate will be discussed herein below.

Figure 3:
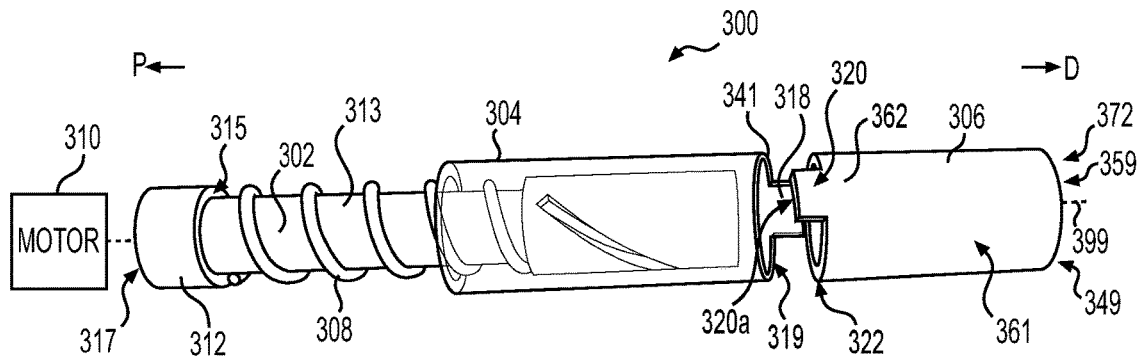
FIG. 3 illustrates a side view of a torque amplification system, according to aspects of this disclosure.
Figure 5:
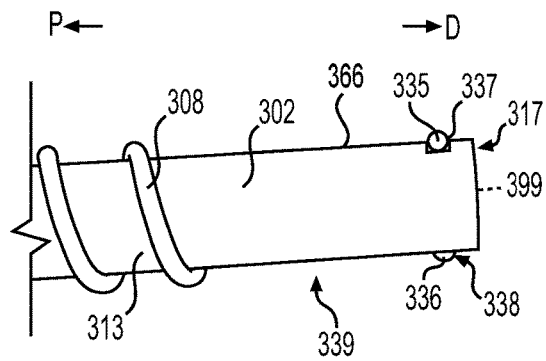

FIG. 3 illustrates a torque amplification system 300 configured for use within a medical device, such as an endoscopic medical device for insertion into a patient's body. System 300 includes a driveshaft 302, a hammer 304, an anvil 306, a spring 308, and a central lumen 372. Central lumen 372 may extend through the entire length of torque amplification system 300. A central longitudinal axis 399 may extend longitudinally through a central portion of system 300. Driveshaft 302 may be positioned at a proximal end of system 300, may be cylindrical, and may be coupled to motor 310. A proximal portion 312 of driveshaft 302 may protrude radially-outward from axis 399 relative to a distal portion 313 of driveshaft 302, and proximal portion 312 may form a shelf 315. Shelf 315 may be configured to be coupled to spring 308, and/or shelf 315 may support a proximal end of spring 308. A central lumen 317 may extend through driveshaft 302 in the proximal-distal direction. A distal end 339 (shown in FIG. 5) of driveshaft 302 may be positioned within a central lumen 319 of hammer 304. As shown in FIG. 5, distal end 339 of driveshaft 302 may include ball bearings 335, 336 positioned within recesses 337, 338 of driveshaft 302. Each ball bearing 335, 336 may extend radially-outward, relative to axis 399, from a radially-outermost surface 366 of driveshaft 302. FIG. 5 illustrates distal end 339 of driveshaft 302 with ball bearings 335, 336 positioned within recesses 337, 338. In some examples, driveshaft 302 may be a part of motor 310, and in other examples driveshaft 302 may be separate from motor 310 and either directly coupled to motor 310 or indirectly coupled to motor 310. In these examples, motor 310 may drive the movement (i.e., rotational movement about axis 399) of driveshaft 302).

Spring 308 may be helical, may include a central lumen that receives distal portion 313 of driveshaft 302, and may extend circumferentially around driveshaft 302. Spring 308 may be coupled to or otherwise abut shelf 315 at a proximal end of spring 308 and may extend longitudinally along a radial exterior of at least a portion of driveshaft 302. In some examples, spring 308 may be coupled to or otherwise abut a proximal end of a tube 314, and in other examples spring 308 may not be coupled to the proximal end of tube 314. Spring 308 may be compressible such that spring 308 may move relative to driveshaft 302 in the proximal direction and the distal direction. For example, distal movement of tube 314 relative to driveshaft 302 may expand spring 308, and proximal movement of tube 314 relative to driveshaft 302 may compress spring 308. Axis 399 may extend longitudinally through a center of spring 308. Spring 308 may be any suitable material, such as Nitinol or any other suitable shape-memory material.

Hammer 304 is shown as transparent in FIG. 3 to illustrate tube 314 within hammer 304. Tube 314 may be an inner tubular portion of hammer 304. Hammer 304 may be cylindrical and may have a uniform diameter along the entire length of hammer 304. Hammer 304 may include a central longitudinal lumen 319 extending through the entire length of hammer 304. Lumen 319 may be configured to receive a tube 314 (shown in FIG. 4), driveshaft 302, and spring 308; and driveshaft 302 and spring 308 may freely move through lumen 319 in the proximal direction and distal direction (i.e., without contacting any internal projections or obstructions within lumen 319). Hammer 304 may include a flange 318 protruding distally from a distal face 341 of hammer 304. Flange 318 may be rectangular in shape, and may have a distalmost edge substantially parallel to distal face 341. Although hammer 304 is shown in FIG. 3 with only one flange 318, hammer 304 is not so limited and may include two, three, four, five, six, seven, eight, or any other suitable number of flanges 318. In some examples, flange 318 may include one or more edges angled relative to central longitudinal axis 399, such as an edge that is transverse to central longitudinal axis 399. Hammer 304 may be made of metal, plastic, or any other suitable material.

Anvil 306 may be cylindrical and may have a central, longitudinal lumen 349 extending longitudinally through anvil 306. Anvil 306 may have a diameter approximately the same as hammer 304, or may have a different diameter than hammer 304; and diameter of anvil 306 may remain constant across the entire longitudinal length of anvil 306. The anvil 306 and hammer 304 overlap in the radial direction, such that movement of anvil 306 proximally caused anvil to contact hammer 304. Anvil 306 may have a flange 320 extending proximally from a proximal face 322 of anvil 306. Flange 320 may be rectangular in shape and may have a proximalmost edge 320a substantially parallel to proximal face 322. Flange 320 may have a radially-outermost surface 362, relative to axis 399, with the same radius of curvature as the radially-outermost surface 361 of anvil 306. Although anvil 306 is shown in FIG. 3 with only one flange 320, anvil 306 is not so limited and may include two, three, four, five, six, seven, eight, or any other suitable number of flanges 320. In some examples, flange 320 may include one or more edges that are angled relative to central longitudinal axis 399, such as an edge that is transverse to central longitudinal axis 399. In some examples, radially-outermost surface 361 may have a constant diameter across the entire longitudinal length of surface 361 from proximal face 322 to distal end face 359.

During operation, flange 318 of hammer 304 may abut proximal face 322 and/or flange 320 of anvil 306. In some examples, flange 318 of hammer 304 may slide across proximal face 322 of anvil 306 and flange 320. Lumen 349 of anvil 306 may be longitudinally aligned with lumen 319 of hammer 304, and lumen 349 may have substantially the same diameter as lumen 319. Anvil 306 may be fixedly coupled to an output shaft (not shown) connected to an end effector, such as grasper 118, end effector 254, or stapler device 201. For example, the output shaft may control opening and closing end effector 254, or may control opening and closing anvil/stapler jaw 220 towards stapler body 222.

Figure 4:
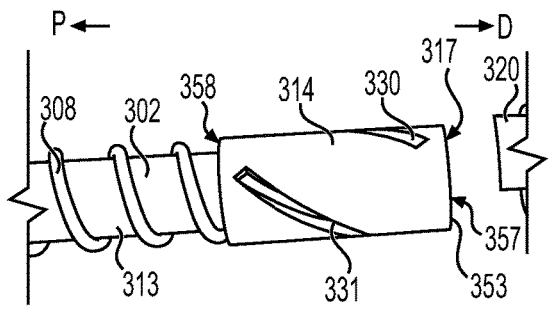
FIGS. 4 and 5 illustrate side views of components of the torque amplification system of FIG. 3, according to aspects of this disclosure.

FIG. 4 illustrates a portion of torque amplification system 300, including driveshaft 302, spring 308, tube 314, and flange 320 of anvil 306. Tube 314 may be fixedly coupled to hammer 304 within lumen 319 such that when tube 314 rotates about axis 399 (FIG. 3) hammer 304 also rotates. In some examples, tube 314 may be welded to hammer 304. Tube 314 may include a longitudinal lumen 357, and lumen 357 may be configured to receive driveshaft 302. In some examples, lumen 357 may have a diameter substantially the same as the diameter of driveshaft 302. Tube 314 may include spiral-cut channels 330, 331 extending longitudinally from a proximal portion to a distal portion of tube 314, and each of spiral-cut channels 330, 331 may extend transverse to axis 399. Each channel 330, 331 may be configured to receive a ball bearing 335, 336 such that each ball bearing 335, 336 may move within one of channels 330, 331.

Channels 330, 331 may be curved and may have closed proximal and distal ends, with each channel 330, 331 terminating proximal to the distalmost end of tube 314 and distal to the proximalmost end of tube 314.

The radially-outermost surface of tube 314 may be spaced the same distance from axis 399 as the radially-outermost surface of proximal portion 312 of driveshaft 302. In some examples, spring 308 may be fixedly coupled to a proximal face 358 of tube 314. In other examples, spring 308 may abut proximal face 358 and may not be fixedly coupled to proximal face 358. Tube 314 may be configured to compress spring 308 when tube 314 moves proximally over driveshaft 302. In some examples, tube 314 may be coupled to hammer 304 such that a distalmost end 353 of tube 314 is positioned proximal from distal face 341 of hammer 304 (FIG. 3). Since lumens 317, 319, 349 are all longitudinally aligned, torque amplification system 300 includes a central longitudinal lumen 372 (FIG. 3) extending the entire length of torque amplification system, which may enable one or more tools or other devices to pass through central longitudinal lumen 372 during operation of torque amplification system 300.

In operation, torque amplification system 300 may deliver pulsed rotations of hammer 304 where energy supplied by motor 310 through driveshaft 302 is stored in spring 308 and then released through hammer 304 rotating and delivering a burst of high torque to anvil 306 (and the output shaft). Accordingly, motor 310 may supply a low amount of torque and the output to anvil 306 may be a high amount of torque. The operation of torque amplification system 300 will be discussed in further detail below with regard to FIGS. 6-10. In describing the operation of torque amplification system 300, direction 601 is a rotational direction counter-clockwise about central longitudinal axis 399 if you are facing the distal end face 359 of anvil 306, and direction 602 is a rotational direction clockwise about central longitudinal axis 399 if you are facing the distal end face 359 of anvil 306.

Figure 6:
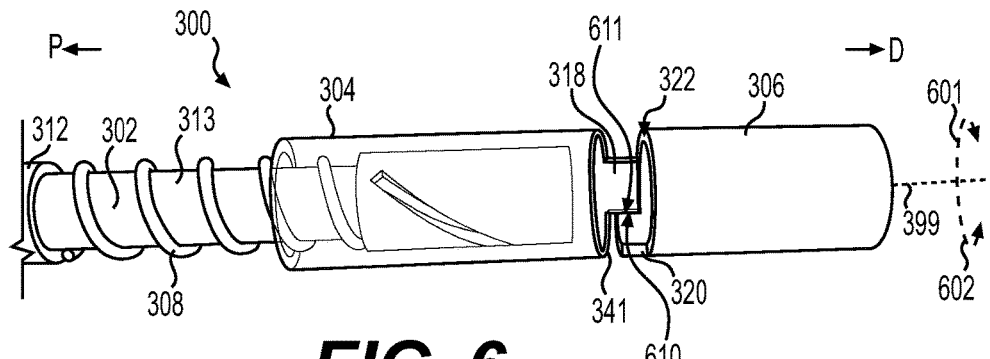
FIGS. 6, 7, and 8 illustrate side views of the torque amplification system of FIG. 3 at various states during operation, according to aspects of this disclosure.

FIG. 6 illustrates a start of a cycle of operation of torque amplification system 300. In FIG. 6, a first edge 611 of flange 318 of hammer 304 abuts a first edge 610 of flange 320 of anvil 306, and hammer 304 is prevented from rotating due to an applied load at the output shaft (not shown) coupled to the anvil 306. In this example, driveshaft 302 is rotating in rotational direction 602. Driveshaft 302 continues to rotate in direction 602, while anvil 306 remains stationary due to the applied load. As driveshaft 302 continues to rotate and anvil 306 remains stationary, hammer 304 moves in the proximal direction, and spring 308 compresses as each of ball bearings 335, 336 (FIG. 5) move distally through each of channels 330, 331, respectively. As hammer 304 moves proximally, first edge 611 retracts proximally and slides across first edge 610. Furthermore, as hammer 304 moves proximally, energy is being stored in compressed spring 308.

Figure 7:
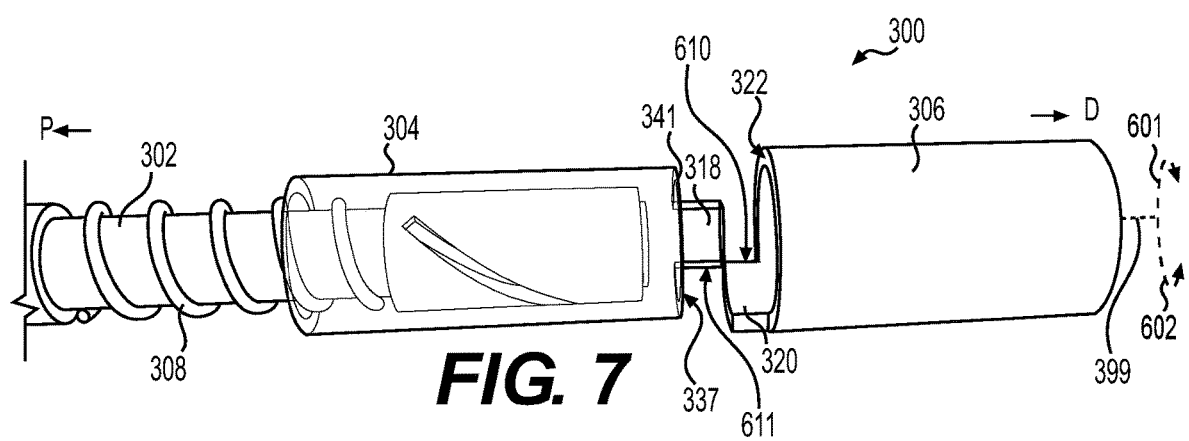

FIG. 7 illustrates hammer 304 in a position in which flange 318 has reached the proximal end of flange 320, with spring 308 in a compressed position from the movement of hammer 304 in a proximal direction. When first edge 611 of flange 318 disengages with first edge 610 of flange 320, hammer 304 rotates in direction 602 about axis 399 and flange 318 moves across the proximal end of flange 320. Once flange 318 releases from flange 320, hammer 304 builds up rotational speed from the release of the stored energy in spring 308 and hammer 304 is pushed in a distal direction by spring 308 as spring 308 expands towards the distal direction. Also at this time when flange 318 releases from flange 320, ball bearings 335, 336 move within channels 330, 331 at a higher speed than the speed of rotation of driveshaft 302. At this point, flange 318 moves distally and abuts proximal face 322 of anvil 306, hammer 304 rotates in direction 602 around axis 399, and flange 318 applies rotational force to flange 320 via both force applied by driveshaft 302 and force applied by spring 308. Since both force from the driveshaft 302 and force from the spring 308 are applied to hammer 304, the amount of force hammer 304 applies to anvil 306 is increased relative to just the driveshaft 302 applying force to anvil 306.

Figure 8:
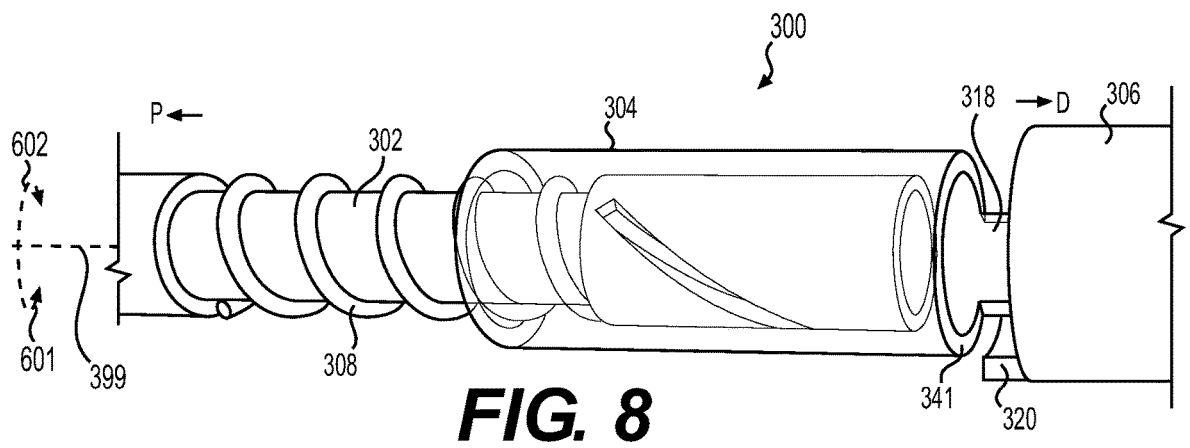

FIG. 8 illustrates torque amplification system 300 after the completion of a cycle of operation of torque amplification system 300, and the process starts over again. In FIG. 8, flange 318 abuts flange 320 and spring 308 is in an expanded state. Torque amplification system 300 may provide a rotational power output larger than the rotational power output supplied by the motor 310 alone.

Figure 9:
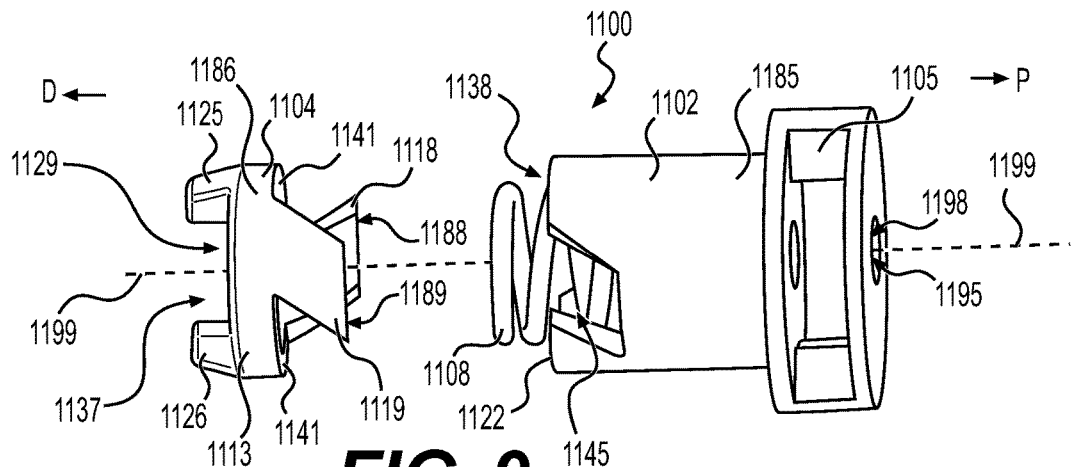
FIG. 9 illustrates a side view of a partially-disassembled torque amplification system, according to aspects of this disclosure.

FIG. 9 illustrates a side, partially exploded view of another embodiment of a torque amplification system 1100. Note the proximal P and distal D directions are flipped relative to previous figures (i.e. proximal is on the right and distal on the left, compared to proximal on the left and distal on the right in previous figures). As shown in FIG. 9, torque amplification system 1100 may include a driveshaft 1102, a gear assembly 1105 such as a spring 1108, a hammer 1104, a central lumen 1198, and a central longitudinal axis 1199. Extra torque converts a very high speed input motor to a lower speed with high torque, enough to turn and compress the spring 1108, and protects the motor from shocks caused by the hammer 1104 action. An anvil 1106 of torque amplification system 1100 is shown in FIG. 11. Spring 1108 may be positioned within a recess 1138 extending longitudinally through driveshaft 1102 from a distalmost end face 1122 of driveshaft 1102. Recess 1138 may be substantially cylindrical and may terminate at proximal end 1142 (shown in FIG. 10). In some examples, driveshaft 1102 may be fixedly coupled to gear assembly 1105 at a proximal end of driveshaft 1102, for example gear assembly 1105 may be integrally formed with driveshaft 1102. Driveshaft 1102 includes two channels 1145, 1146 extending proximally from distalmost end face 1122 of driveshaft 1102. Each channel 1145, 1146 may extend at an angle relative to central longitudinal axis 1199, and channel 1145 may be positioned at an opposite side of central longitudinal axis 1199 from channel 1146. A central lumen 1195 may extend through driveshaft 1102.

Hammer 1104 may include a central lumen 1137 extending longitudinally through hammer 1104, a cylindrical body 1113, two proximally-extending protrusions 1118, 1119, and two flanges 1125, 1126 extending distally from a distal face 1129 of cylindrical body 1113. Each protrusion 1118, 1119 may protrude proximally from a proximal face 1141 of cylindrical body 1113, and each protrusion 1118, 1119 may be angled relative to longitudinal axis 1199, for example, at a same or similar angle as the angle of channels 1145, 1146 relative to longitudinal axis 1199, respectively. Protrusion 1118 may be positioned at an opposite side of axis 1199 from protrusion 1119, and protrusion 1118 may be angled transverse from protrusion 1119. Each protrusion 1118, 1119 may include a proximally-facing front face 1188, 1189, respectively, and each proximally-facing front face 1188, 1189 may be substantially perpendicular to central longitudinal axis 1199. Each protrusion 1118, 1119 may be configured to be received by each channel 1145, 1146. Each flange 1125, 1126 may be approximately ninety-degrees offset from each protrusion 1118, 1119. A radially-outermost surface 1186 of hammer 1104 may be spaced from axis 1199 the same distance as a radially-outermost surface 1185 of driveshaft 1102, such that driveshaft 1102 and hammer 1104 have a uniform diameter.

Figure 10:
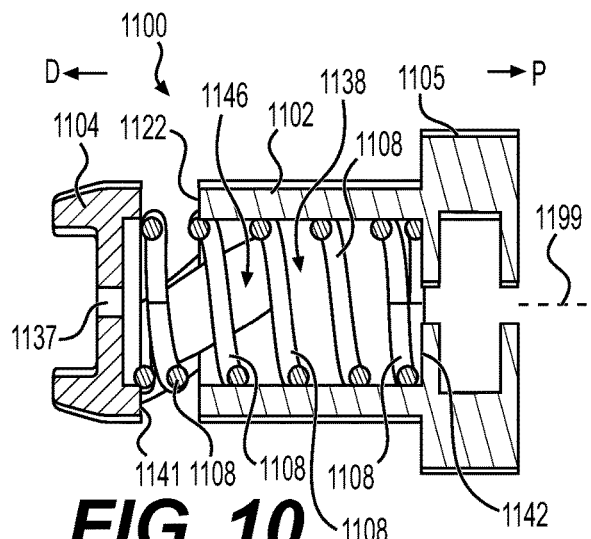
FIG. 10 illustrates a side, cross-sectional view of the torque amplification system of FIG. 9 in an assembled state, according to aspects of this disclosure.
Figure 11:
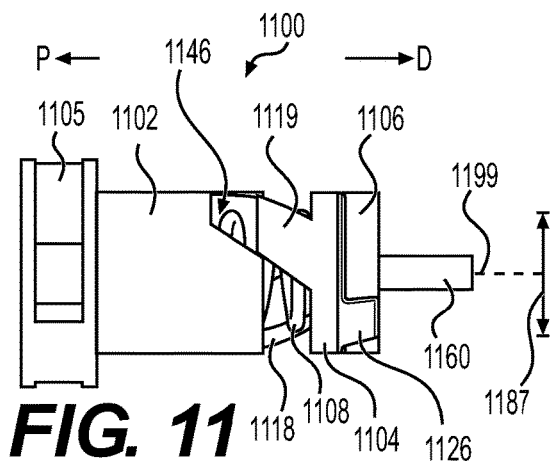
FIG. 11 illustrates a side view of the torque amplification system of FIG. 9 in an assembled state, according to aspects of this disclosure.

FIG. 10 illustrates a side, cross-sectional view of torque amplification system 1100 including driveshaft 1102, gear assembly 1105, hammer 1104, and spring 1108. As shown in FIG. 10, spring 1108 may be coupled to or abut driveshaft 1102 at a proximal end 1142 of recess 1138 and may be coupled to or abut hammer 1104 at proximal face 1141 of hammer 1104. Spring 1108 may expand and contract within recess 1138, and may move proximally or distally through recess 1138, along longitudinal axis 1199.

FIG. 11 illustrates a side view of torque amplification system 1100 including driveshaft 1102, gear assembly 1105, hammer 1104, spring 1108, anvil 1106, and output shaft 1160. Output shaft 1160 may have a radially-outer surface 1164. As shown in FIG. 11, hammer 1104 abuts driveshaft 1102 when torque amplification system 1100 is in a fully assembled state, and protrusions 1118, 1119 are positioned partially within channels 1145, 1146, respectively. FIG. 11 illustrates torque amplification system 1100 when spring 1108 is in an equilibrium state and not storing energy. Spring 1108 is contained within and/or between driveshaft 1102 and hammer 1104, and protrusions 1118, 1119 may move into and out of channels 1145, 1146 during operation of torque amplification system 1100. Anvil 1106 may be coupled to an output shaft 1160, and output shaft 1160 may longitudinally extend distally along axis 1199 from anvil 1106. Driveshaft 1102, hammer 1104, and anvil 1106 may all have a uniform diameter 1187 about axis 1199, which may facilitate positioning torque amplification system 1100 within a smaller space, such as within an endoscopic catheter.

Figure 12:
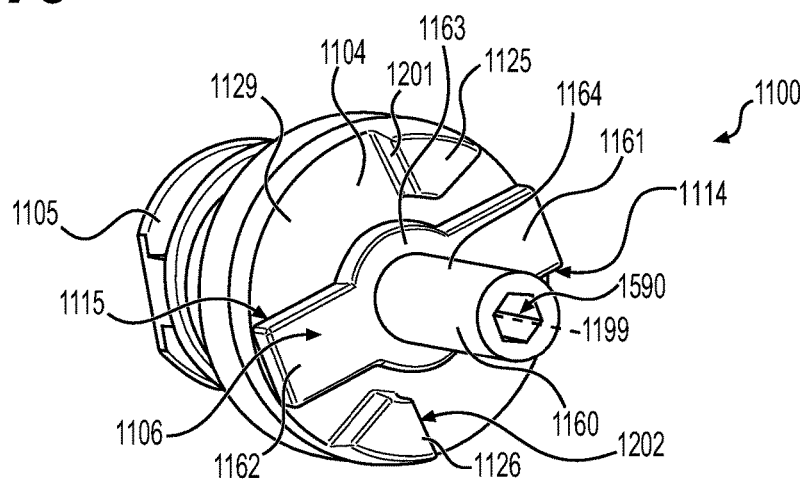
FIG. 12 illustrates a perspective view of the torque amplification system of FIG. 9 in an assembled state, according to aspects of this disclosure.

FIG. 12 illustrates a perspective view of torque amplification system 1100 showing anvil 1106 abutting distal end face 1129 of hammer 1104. Anvil 1106 may be T-shaped and may include a central portion 1163, a first lateral portion 1161, a second lateral portion 1162, and a central lumen 1590. Central portion 1163 may be generally cylindrical, and central lumen 1590 may extend through a center of central portion 1163. First lateral portion 1161 may extend radially-outward, relative to axis 1199, from central portion 1163; and second lateral portion 1162 may extend radially-outward, relative to axis 1199, from central portion 1163 at an opposite side of central portion 1163 from first lateral portion 1161. Output shaft 1160 may be fixedly coupled to anvil 1106, for example, via the central lumen, and output shaft 1160 may include a central lumen 1590 extending longitudinally through at least a portion of output shaft 1160. As shown in FIG. 12, central lumen 1590 may include one or more flat internal surfaces, for example, six flat surfaces forming a substantially hexagonal lumen. Each flange 1125, 1126 may be configured to engage anvil 1106 such that, when flanges 1125, 1126 abut anvil 1106, flanges 1125, 1126 may impart rotational force to anvil 1106 to rotate output shaft 1160.

In operation, torque amplification system 1100 may deliver pulsed rotations of hammer 1104 where energy supplied by a motor through driveshaft 1102 is stored in spring 1108 and then released through hammer 1104 rotating and delivering a burst of high torque to anvil 1106 and the output shaft 1160, in the same manner described above in relation to torque amplification system 300. In describing the operation of torque amplification system 1100, direction 1301 is a rotational direction counter-clockwise about central longitudinal axis 1199 if you are facing the distal end face 1129 of hammer 1104, and direction 1302 is a rotational direction clockwise about central longitudinal axis 1199 if you are facing the distal end face 1129 of hammer 1104.

Figure 13:
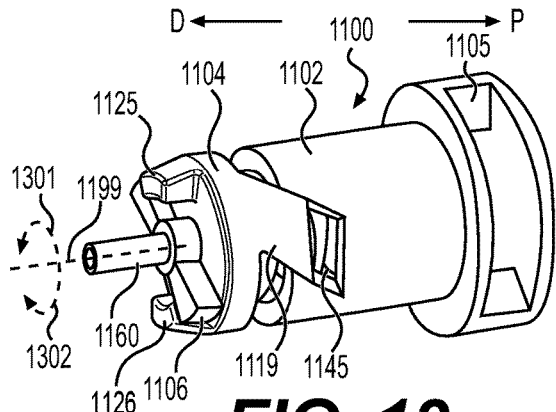
FIGS. 13 and 14 illustrate perspective and side views of the torque amplification system of FIG. 9, according to aspects of this disclosure.

A start of a cycle of operation of torque amplification system 1100 may begin when each of a first edges 1201, 1202 of flanges 1125, 1126 abuts a first edge 1114 of first lateral portion 1161 and a second edge 1115 of second lateral portion 1162, respectively, of anvil 1106. This position is shown in FIG. 13. Hammer 1104 is prevented from rotating due to an applied load at output shaft 1160 coupled to anvil 1106. In this example, driveshaft 1102 is rotating in rotational direction 1302. Driveshaft 1102 continues to rotate in direction 1302, while anvil 1106 remains stationary due to the applied load. As driveshaft 1102 continues to rotate and anvil 1106 remains stationary, hammer 1104 moves in the proximal direction and spring 1108 compresses as each of protrusions 1118, 1119 move proximally into each of channels 1146, 1146, respectively. As hammer 1104 moves proximally, energy is being stored in spring 1108 as spring 1108 compresses.

Figure 14:
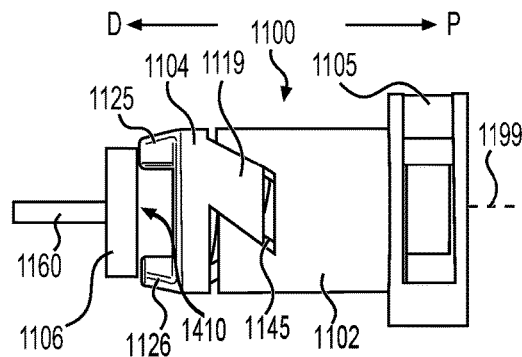

FIG. 14 illustrates hammer 1104 in a position in which flanges 1125, 1126 have reached the proximal end 1410 of anvil 1106, with spring 1108 in a compressed position from the movement of hammer 1104 in a proximal direction. When first edge 1201 of flange 1125 disengages with second edge 1115 of anvil 1106 and second edge 1202 of flange 1126 disengages with first edge 1114 of anvil 1106, hammer 1104 rotates in direction 1301 about axis 399. Flange 1125 then moves across the proximal end of lateral portion 1162 and flange 1126 moves across the proximal end of lateral portion 1161. Once flanges 1125, 1126 release from anvil 1106, hammer 1104 builds up rotational speed from the release of the stored energy in spring 1108 and hammer 1104 is pushed in a distal direction by spring 1108 as spring 1108 expands towards the distal direction. Also at this time, when flanges 1125, 1126 release from anvil 1106, protrusions 1118, 1119 move within channels 1145, 1146 at a higher speed than the speed of rotation of driveshaft 1102. At this point, flanges 1125, 1126 move distally and distal face 1129 of hammer abuts anvil 1106, hammer 1104 rotates in direction 1301 around axis 1199, and flanges 1125, 1126 apply rotational force to anvil 1106 via both force applied by driveshaft 1102 and force applied by spring 1108. Since both force from the driveshaft 1102 and force from the spring 1108 are applied to hammer 1104, the amount of force hammer 1104 applies to anvil 1106 is increased relative to just the driveshaft 1102 applying force to anvil 1106. By utilizing protrusions 1118, 1119 of hammer 1104 and channels 1145, 1146 driveshaft, the overall size, for example, overall diameter, of torque amplification system 1100 may be decreased, which may facilitate positioning torque amplification system 1100 within a medical device such as an endoscopic medical device.

Figure 15:
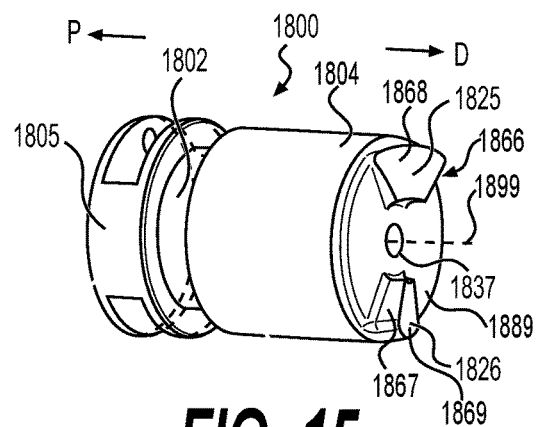
FIG. 15 illustrates a perspective view of a torque amplification system, according to aspects of this disclosure.

FIG. 15 illustrates a perspective view of another embodiment of a torque amplification system 1800. As shown in FIG. 15, torque amplification system 1800 may include a driveshaft 1802, a gear assembly 1805 such as a planetary gear assembly, a hammer 1804, central lumen 1837, and a central longitudinal axis 1899. Hammer 1804 may be cylindrical and may include two protrusions 1825, 1826 extending outward in a distal direction from a distal end face 1889 of hammer 1804. In some examples, each protrusion 1825, 1826 may include a first surface 1866, 1867 and a second surface 1868, 1869, respectively. Each first surface 1866, 1867 may be configured to engage with anvil 1806. First surfaces 1866, 1867 may be substantially perpendicular to distal end face 1889. Second surfaces 1868, 1869 of protrusions 1825, 1826 may be angled relative to distal end face

Figure 16:
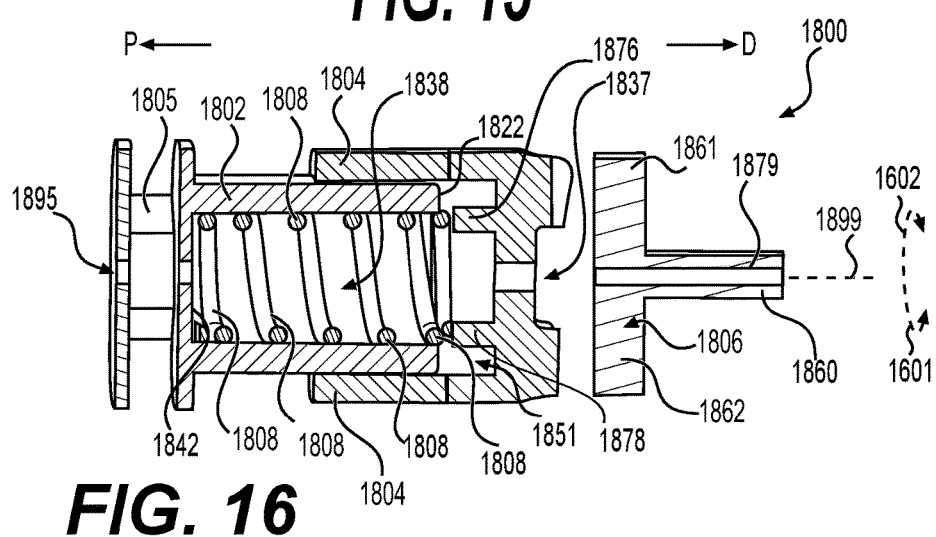
FIG. 16 illustrates a side, cross-sectional view of the torque amplification system of FIG. 15, according to aspects of this disclosure.

1889. Each protrusion 1825, 1826 may be positioned at an outer peripheral region of distal end face 1889, and protrusion 1825 may be positioned at an opposite side of axis 1899 from protrusion 1826. First surface 1866 may face a direction opposite from the direction first surface 1867 faces. As shown in FIG. 16, hammer 1804 may include a central recess 1851 configured to receive driveshaft 1802. Hammer 1804 will be discussed in further detail below with regard to FIGS. 17 and 18.

FIG. 16 illustrates a side, cross-sectional view of torque amplification system 1800, including anvil 1806 and spring 1808. Spring 1808 may be positioned within a recess 1838 extending longitudinally through driveshaft 1802 from distalmost end face 1822. Recess 1838 may be cylindrical and may terminate at proximal end 1842. In some examples, spring 1808 may be fixedly coupled to or otherwise abut proximal end 1842 of driveshaft 1802, and may be fixedly coupled to or otherwise abut distal end portion 1876, 1878 of hammer 1804. Spring 1808 may be moveable within recess 1838 in both proximal and distal directions. For example, spring 1808 may move between a neutral state and a contracted or compressed state, in which spring 1808 may store mechanical energy. Spring 1808 may be longitudinally aligned with axis 1899, and lumen 1837 may extend longitudinally through a central portion of spring 1808.

Driveshaft 1802 may be fixedly coupled to the gear assembly 1805 at a proximal end of driveshaft 1802. A central lumen 1895 may extend longitudinally through driveshaft 1802, and lumen 1895 may open into recess 1838. Driveshaft 1802 may be cylindrical and may be configured to be received by and/or move within recess 1851 of hammer 1804. Driveshaft 1802 may be rotatable about axis 1899 within recess 1851 of hammer 1804. Anvil 1806 may be T-shaped and may be coupled to an output shaft 1860. Anvil 1806 may include a first lateral portion 1861, a second lateral portion 1862, and a lumen 1879 extending longitudinally through anvil 1806 at a central portion of anvil 1806.

Figure 17:
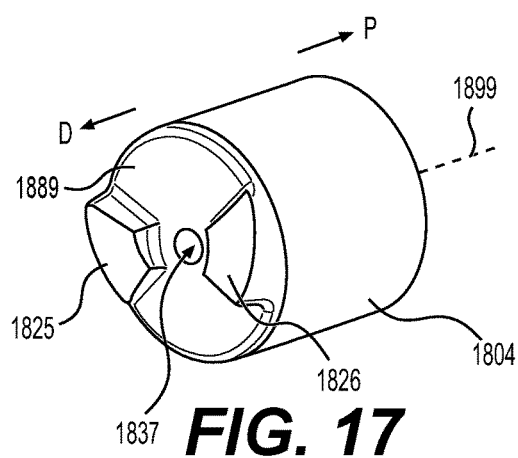
FIGS. 17, 18, and 19 illustrate portions of the torque amplification system of FIG. 15, according to aspects of this disclosure.
Figure 18:
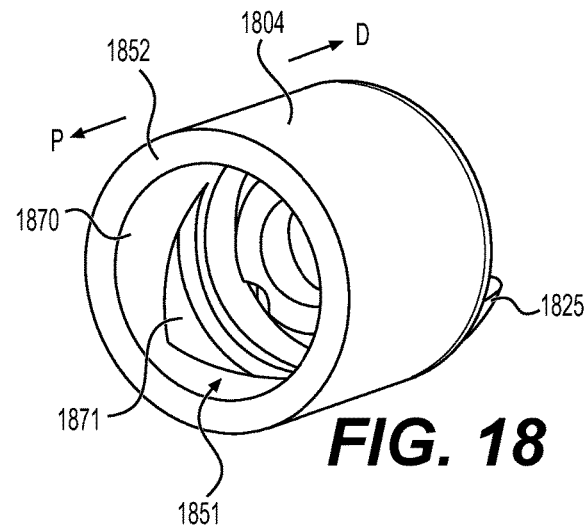
Figure 20:
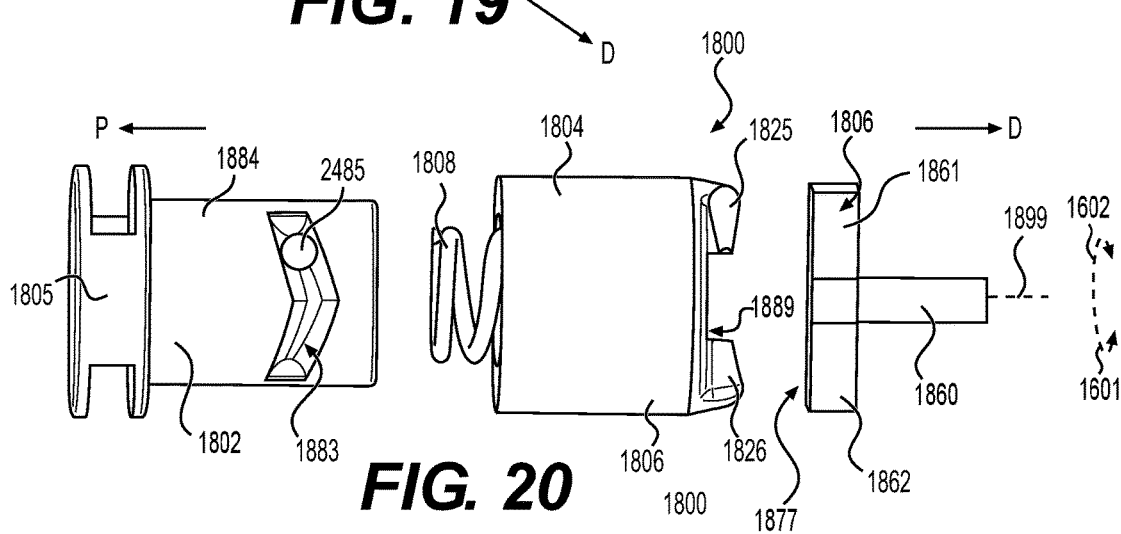
FIG. 20 illustrates a side view of the torque amplification system of FIG. 15 in a partially-disassembled state, according to aspects of this disclosure.

FIGS. 17 and 18 illustrate perspective views of hammer 1804, including protrusions 1825, 1826, recess 1851, central lumen 1837, distal end face 1889, and a proximalmost face 1852. As shown in FIG. 18, recess 1851 may be partially formed by a curved, radially-inward facing surface 1870. Radially-inward facing surface 1870 may include a channel 1871 configured to receive a ball bearing 2485 (FIG. 20). Channel 1871 may be V-shaped, and may be recessed from radially-inward facing surface 1870. Channel 1871 may allow for ball bearing 2485 to move as hammer 1804 is moved relative to driveshaft 1802.

Figure 19:
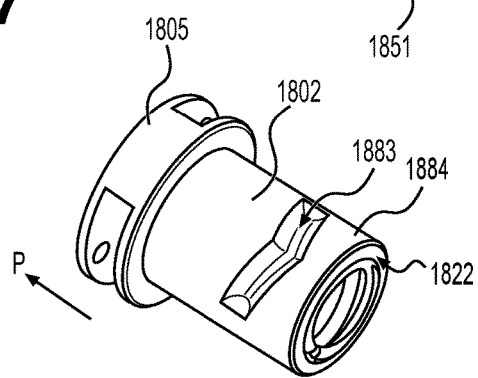

FIG. 19 illustrates a perspective view of driveshaft 1802 including gear assembly 1805 and distal face 1822. As shown in FIG. 19, driveshaft 1802 may include a V-shaped channel 1883 on a radially-outer surface 1884 of driveshaft 1802. Channel 1883 may be configured to receive ball bearing 2485, and channel 1883 may be configured to align with channel 1871 when driveshaft 1802 is positioned within hammer 1804.

FIG. 20 illustrates a side view of torque amplification system 1800 in a partially-disassembled state. In FIG. 20, ball bearing 2485 is positioned within channel 1883, and spring 1808 is positioned within hammer 1804. Ball bearing 2485 combined with both channel 1883 and channel 1871 may facilitate the compression of spring 1808 once a load is applied at anvil 1806. When torque amplification system 1800 is in a fully-assembled state, driveshaft 1802 is positioned within recess 1851 of hammer 1804 and ball bearing 2485 is received by both channel 1883 and channel 1871. Ball bearing 2485 may move within both channel 1883 and channel 1871 when torque amplification system 1800 is in a fully-assembled state. For example, movement of ball bearing 2485 within both channel 1883 and channel 1871 during operation of torque amplification system 1800 may allow hammer 1804 to translate proximally relative to driveshaft 1802 and compress spring 1808.

A start of a cycle of operation of torque amplification system 1800 may begin when each of first surfaces 1866, 1867 abut anvil 1806. Hammer 1804 is prevented from rotating due to an applied load at output shaft 1860 coupled to anvil 1806. In this example, driveshaft 1802 is rotating in rotational direction 1602, or clockwise about axis 1899 when facing distal end face 1889 of hammer 1804 when the viewer is on the right side of the page, and rotational direction 1601 is opposite direction 1602. Driveshaft 1802 continues to rotate in direction 1602 while anvil 1806 remains stopped due to the applied load. As driveshaft 1802 continues to rotate and anvil 1806 remains stationary, hammer 1804 moves in the proximal direction, relative to driveshaft 1802, and spring 1808 compresses as each of protrusions 1825, 1826 move proximally away from anvil 1806. As hammer 1804 moves proximally, energy is being stored in spring 1808.

When protrusions 1825, 1826 reach a proximal end 1877 of anvil 1806, with spring 1808 in a compressed state from the movement of hammer 1804 in a proximal direction, protrusions 1825, 1826 move across proximal end 1877 of anvil 1806 and hammer 1804 rotates in direction 1602 about axis 1899. Once hammer 1804 releases from anvil 1806, hammer 1804 builds up rotational speed from the release of the stored energy in spring 1808, and hammer 1804 is moved in a distal direction by spring 1808 as spring 1808 expands towards the distal direction. Also at this time when hammer 1804 releases from anvil 1806, ball bearing 2485 moves within channels 1871, 1883 at a higher speed than the speed of rotation of driveshaft 1802. At this point, protrusions 1825, 1826 move distally and distal end face 1889 of hammer 1804 abuts anvil 1806, hammer 1804 rotates in direction 1602 about axis 1899, and protrusions 1825, 1826 apply rotational force to anvil 1806 via both force applied by driveshaft 1802 and force applied by spring 1808. Since both force from the driveshaft 1802 and force from the spring 1808 are applied to hammer 1804, the amount of force hammer 1804 applies to anvil 1806 is increased relative to just the driveshaft 1802 applying force to anvil 1806. Torque amplification system 1800 may provide a rotational power output to actuate a medical device, such as a grasper or stapler device. Positioning spring 1808 within driveshaft 1802 may facilitate building torque amplification system 1800 at a scale sufficiently small to be included within an endoscopic medical device, such as an endoscopic grasper or endoscopic stapler.

FIG. 21 illustrates a side view of another torque amplification system 2400 in a partially disassembled state. Torque amplification system 2400 may include a driveshaft 2402, a hammer 2404 including a recess 2451 and protrusions 2425, 2426, an anvil 2406, spring 2408, an output shaft 2461, a central longitudinal lumen 2460, a ball bearing 2435, a gear assembly 2405 (e.g. a planetary gear assembly), and a central longitudinal axis 2499. Torque amplification system 2400 may include any of the features described above in relation to torque amplification system 1800, and may operate in the same manner described above in relation to torque amplification system 1800. Spring 2408 may have a conical shape including a proximal end 2475 and a distal end 2476. Proximal end 2475 may have a larger diameter about axis 2499 than the diameter of distal end 2476 about axis

2499. As can be seen in the side, cross-sectional view of torque amplification system 2400 of FIG. 22, proximal end 2475 may be fixedly coupled to the inside of driveshaft 2402, for example at proximal end 2442 of recess 2451. Distal end 2476 may be fixedly coupled inside hammer 2404 at a proximal portion 2443 of hammer 2404 within a recessed portion 2452, or in some examples distal end 2476 may abut recessed portion 2452. The conical shape of spring 2408 may allow spring 2408 to be both compressed longitudinally and also twisted about axis 2499 during operation of torque amplification system 2400.

Any of the torque amplification systems 300, 1100, 1800, 2400 may include a ratchet mechanism, such as incorporating a ratchet mechanism at motor 310 or driveshaft 302, 1102, 1802, 2402. A ratchet mechanism may prevent slip-back during operation of torque amplification systems 300, 1100, 1800, 2400 and may facilitate maintaining a closed or shut position during operation of a grasper, forceps, and/or an endoscopic stapler device.

It also should be understood that one or more aspects of any of the medical devices, systems, and methods described herein may be used for cutting, dissecting, treating, stapling, grasping, or ablating tissue in any part of the human body. For example, any of the medical devices described herein may be used in medical procedures such as for Endoscopic Submucosal Dissection (ESD), cancer treatment, and/or other procedures where removal, dissection, fulguration, stapling, fastening, grasping, moving, and/or ablation of the type of tissue is needed.

Various aspects discussed herein may help reduce procedure time, increase tissue treatment effectiveness, reduce the risks to the subject, etc.

Although the exemplary embodiments described above have been disclosed in connection with medical devices for manipulating and resecting human tissue through the working channel of a medical device, a natural orifice, or by incision, a person skilled in the art will understand that the principles set out above can be applied to any medical device or medical method and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of this disclosure and can be envisioned and implemented by those of skill in the art.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

Other exemplary embodiments of this disclosure will be apparent to those skilled in the art from consideration of the specification and practice of the exemplary embodiments disclosed herein. It is intended that the specification and examples be considered as exemplary only, and departures in form and detail may be made without departing from the scope and spirit of this disclosure as defined by the following claims.

We claim:

1. A medical device comprising:
   a main shaft extending from a proximal end to a distal end;
   an actuator at a proximal portion of the medical device;
   an end effector positioned at a distal end of the main shaft and comprising a first jaw and a second jaw;
   a motor; and
   a torque amplification system comprising:
      a driveshaft coupled to the motor;
      a spring coupled to the driveshaft and configured to expand or contract in a proximal or a distal direction relative to the driveshaft;
      a hammer moveably coupled to the driveshaft; and
      an anvil coupled to the end effector and abutting the hammer, wherein the anvil is configured to provide a rotational power output to the end effector to move the first jaw and/or the second jaw.

2. The medical device of claim 1, wherein the motor is positioned within a distal portion of the main shaft.

3. The medical device of claim 1, further comprising a handle coupled to the proximal end of the main shaft, wherein the actuator is positioned on the handle.

4. The medical device of claim 1, wherein the end effector is an endoscopic stapler, a grasper, forceps, or scissors.

5. The medical device of claim 1, wherein:
   the hammer includes a first flange extending distally from a distal face of hammer;
   the anvil includes a second flange extending proximally from a proximal face of the anvil; and
   the first flange is configured to engage the second flange to rotate anvil about a central longitudinal axis of the anvil.

6. The medical device of claim 5, wherein:
   the hammer is cylindrical and includes an inner tubular portion;
   the inner tubular portion includes a channel extending transverse to a central longitudinal axis of the hammer;
   the driveshaft includes a ball bearing coupled to a distal end of the driveshaft; and
   the ball bearing is movably positioned within the channel.

7. The medical device of claim 6, wherein the spring extends circumferentially around a radially-outer surface of the driveshaft and abuts a proximal end of the inner tubular portion.

8. The medical device of claim 7, wherein the torque amplification system further comprises a central, longitudinal lumen extending through the driveshaft, the hammer, the spring, and the anvil.

9. The medical device of claim 1, wherein each of the hammer and the anvil is cylindrical; and wherein the hammer has a diameter substantially the same as the diameter of the anvil.

10. The medical device of claim 1, wherein:
   the driveshaft includes (i) a recess extending longitudinally through the driveshaft from a distal end of the driveshaft, and (ii) a pair of channels extending proximally from the distal end;
   the spring is positioned with the recess; and the hammer includes (i) a pair of protrusions extending proximally from a proximal face of the hammer, wherein each of the pair of protrusions are configured to be received by each of the pair of channels, respectively; and (ii) a pair of flanges extending distally from a distal end face of hammer.

11. The medical device of claim 10, wherein the anvil is T-shaped.

12. The medical device of claim 1, wherein:
the driveshaft includes a first recess;
the hammer includes a second recess and a pair of protrusions extending distally from a distal face of the hammer;
the spring is positioned within the first recess and a distal end of the spring is fixedly coupled to a proximally-facing surface within the second recess; and
a distal portion of the driveshaft is received within the second recess.

13. The medical device of claim 12, wherein:
the hammer includes a first channel within the second recess;
the driveshaft includes a second channel in a radially-outward surface, relative to a central longitudinal axis, of the driveshaft; and
a ball bearing is positioned between the first channel and the second channel.

14. The medical device of claim 12, wherein the spring is conical.

15. The medical device of claim 1, further comprising a ratchet mechanism coupled to the driveshaft.

16. A medical device comprising:
an end effector; and
a torque amplification system comprising:
 a driveshaft coupled to the motor;
 a spring coupled to the driveshaft and configured to expand or contract in a proximal or a distal direction relative to the driveshaft;
 a hammer moveably coupled to the driveshaft;
 an anvil coupled to an output shaft and abutting the hammer, wherein the anvil is configured to provide a rotational power output to the output shaft; and
 a lumen extending along a central longitudinal axis of the torque amplification system, wherein the lumen extends through the driveshaft, the spring, the hammer, and the anvil;
wherein the output shaft is coupled to the end effector.

17. The medical device of claim 16, wherein:
the hammer is cylindrical and includes an inner tubular portion;
the inner tubular portion includes a channel extending transverse to a central longitudinal axis of the hammer;
the driveshaft includes a ball bearing coupled to a distal end of the driveshaft;
the ball bearing is movably positioned within the channel; and
the spring extends circumferentially around a radially-outer surface of the driveshaft and abuts a proximal end of the inner tubular portion.

18. The medical device of claim 16, wherein:
the driveshaft includes (i) a recess extending longitudinally through the driveshaft from a distal end of the driveshaft, and (ii) a pair of channels extending proximally from the distal end of the driveshaft;
the spring is positioned with the recess; and
the hammer includes (i) a pair of protrusions extending proximally from a proximal face of the hammer, wherein each of the pair of protrusions are configured to be received by each of the pair of channels, respectively; and (ii) a pair of flanges extending distally from a distal end face of hammer.

19. The medical device of claim 16, wherein:
the driveshaft includes a first recess;
the hammer includes a second recess, a pair of protrusions extending distally from a distal face of hammer, and a first channel within the second recess;
the spring is positioned within the first recess and a distal end of the spring is fixedly coupled to a proximally-facing surface within the second recess;
a distal portion of the driveshaft is received within the second recess;
the driveshaft includes a second channel in a radially-outward surface, relative to a central longitudinal axis, of the driveshaft; and
a ball bearing is movably positioned between the first channel and the second channel.

20. A medical device comprising:
a shaft extending longitudinally from a proximal end portion to a distal end portion;
a motor positioned within the distal end portion;
an end effector at the distal end portion; and
a torque amplification system comprising:
 a driveshaft coupled to the motor;
 a spring coupled to the driveshaft and configured to move relative to the driveshaft;
 a hammer moveably coupled to the driveshaft; and
 an anvil coupled to the end effector and abutting the hammer, wherein the anvil is configured to provide a rotational power output to the end effector.

* * * * *